(12) United States Patent
Drapeau et al.

(10) Patent No.: US 8,758,806 B2
(45) Date of Patent: Jun. 24, 2014

(54) HUMAN LUBRICATION GEL

(75) Inventors: Susan J. Drapeau, Cordova, TN (US); Guobao Wei, Milltown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/355,712

(22) Filed: Jan. 23, 2012

(65) Prior Publication Data

US 2013/0189344 A1 Jul. 25, 2013

(51) Int. Cl.
| | |
|---|---|
| A61K 38/39 | (2006.01) |
| A61K 9/14 | (2006.01) |
| A61K 9/50 | (2006.01) |
| A61K 9/70 | (2006.01) |
| A61P 29/00 | (2006.01) |
| A61P 19/08 | (2006.01) |
| A61P 21/02 | (2006.01) |
| A61P 19/02 | (2006.01) |
| B82Y 5/00 | (2011.01) |

(52) U.S. Cl.
USPC .......... 424/443; 424/489; 424/400; 514/17.2; 977/795; 977/906

(58) Field of Classification Search
None
See application file for complete search history.

(56) References Cited

U.S. PATENT DOCUMENTS

| | | | |
|---|---|---|---|
| 4,624,255 A | 11/1986 | Scheneck et al. | |
| 4,863,457 A | 9/1989 | Lee | |
| 5,522,844 A | 6/1996 | Johnson | |
| 5,868,789 A | 2/1999 | Huebner | |
| 6,632,457 B1 * | 10/2003 | Sawhney | 424/501 |
| 6,756,058 B2 | 6/2004 | Brubaker et al. | |
| 6,974,462 B2 | 12/2005 | Sater | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,318,840 B2 | 1/2008 | McKay | |
| 7,329,259 B2 | 2/2008 | Cragg | |
| 7,361,168 B2 | 4/2008 | Makower et al. | |
| 7,367,978 B2 | 5/2008 | Drewry et al. | |
| 2006/0106361 A1 | 5/2006 | Muni et al. | |
| 2006/0259119 A1 | 11/2006 | Rucker | |
| 2007/0185497 A1 | 8/2007 | Cauthen et al. | |
| 2007/0202190 A1 * | 8/2007 | Borden | 424/549 |
| 2007/0243225 A1 | 10/2007 | McKay | |
| 2007/0243228 A1 * | 10/2007 | McKay | 424/426 |
| 2009/0263319 A1 * | 10/2009 | Wohabrebbi et al. | 424/1.61 |
| 2010/0015196 A1 | 1/2010 | Kimble et al. | |

* cited by examiner

Primary Examiner — Brian Gulledge
Assistant Examiner — Celeste A Roney
(74) Attorney, Agent, or Firm — Sorell Lenna & Schmidt LLP

(57) ABSTRACT

Human lubricating gels, methods and kits for delivering a therapeutic agent to a target tissue site beneath the skin of a patient utilizing human lubricating gel are provided, the human lubricating gel being capable of adhering to the target tissue site and comprising one or more biodegradable formulations containing an effective amount of the therapeutic agent. In various embodiments, the human lubricating gel is sprayable and hardens after contacting the target tissue site.

19 Claims, 2 Drawing Sheets

HUMAN LUBRICATION GEL

BACKGROUND

It is known that in mammals in general and particularly in man, synovial fluid acts to effectively lubricate the surfaces of bones that are in frictional contact to form joints, as well as lubricating other physiological articulations such as muscles, tendons, ligaments, cartilage or bones which move relative to other muscles, ligaments, tendons, cartilage or bones.

Within a joint cavity, cartilage is the smooth lining that covers the ends of bones where the bones meet to form the joint and that gives the joint freedom of movement by decreasing friction. The cartilage is kept slippery by synovial fluid, joint fluid made by the joint lining (the synovial membrane). The synovial fluid is contained in a soft tissue enclosure around the joints, called the joint capsule. The synovial fluid has a high content of hyaluronic acid (HA) which increases the viscosity of the synovial fluid. Normal synovial fluid contains 3-4 mg/ml of HA. Along with lubricin, HA is one main lubricating components of the synovial fluid.

If the articular cartilage degenerates or erodes, the concentration of HA decreases and the synovial fluid becomes less viscous. The underlying bone becomes uncovered resulting in bone-to-bone contact which causes significant pain. Additionally, as a result of this bone-to-bone contact, small outgrowths called bone spurs, or osteophytes, may form in the joint. Bits of bone or cartilage can break off and float inside the joint space causing more pain and damage.

Many factors may contribute to the development of a cavity or joint condition. They may include a prior injury to a component of the cavity including strains, rupture, and dissection, partial and full tears of the lumen or lining of the cavity, ligaments, tendon, cartilages, meniscus or synovial lining. The cavity or joint may also be affected by an autoimmune disease such as a rheumatoid arthritis or a degenerative disease such as osteoarthritis (OA).

Currently, there are no effective alternatives for treating joint diseases between a temporary pain relief and a surgical intervention. For example, OA affects approximately 21 million Americans a year accounting for 25% of visits to primary care physicians. It is estimated that 80% of the population will have radiographic evidence of OA by age 65 with more than 60% of those exhibiting symptoms. Most people with osteoarthritis use drug therapy to ease the symptoms of the disease. Majority of OA drugs focus mainly on relieving pain, and have little to no effect on slowing or reversing the breakdown of the cartilage. Another approach to treating osteoarthritis, specifically knee osteoarthritis, is an injection into the joint of hylauronic acid ("HA"). Similar to drug therapies, the HA injections provide temporary relief but do not affect the progression of the disease. Finally, if the above methods of OA management are ineffective, a surgical intervention such as total joint replacement is required.

Osteoarthritis is considered to be a disorder characterized by "wear and tear" of a joint, which has often been mechanically abused. It is inherent in osteoarthritis that the lubrication system of the joint is compromised, which results in degeneration of the joint such that it then becomes painful to move, especially under load. In many instances, if the patient restricts or stops using that joint as a result of the inherent pain, the disease process is exacerbated due to the further reduction in joint lubrication by synovial fluids. Other disorders are also characterized by reduced lubrication of joints or other physiological articulations such as situations where muscle, ligament, tendon, cartilage or bone moves relative to other muscle, ligament, tendon, cartilage or bone. Such disorders are often associated with over use or injuries, particularly sporting injuries. It is therefore desirable to develop a lubricant composition and method of utilizing such a composition to improve the lubrication of joints and other physiological articulations in order to keep the joint or articulation mobile and reduce mechanical stress, which often results in pain especially during movement.

It is therefore desirable to provide a lubricant and methods of lubrication would reduce the co-efficient of friction between intra-articular joints and membranes lining the same in order to reduce wear of intra-articular surfaces and initiate and/or enhance motion.

Accordingly, there is a need for an effective therapy that will control or reverse the progression of pathologies associated with intra-articular joints and membranes lining the same.

SUMMARY

New human lubricating gels, compositions including the same and methods of treatment are provided, which can easily allow accurate and precise implantation of human lubricating gel with minimal physical and psychological trauma to a patient. One advantage of drug compositions and methods utilizing human lubricating gel is that the human lubricating gel can now be easily delivered and adheres to the target tissue site (e.g., synovial joint, at or near the spinal column, etc.) using a human lubricating gel that, in some embodiments, hardens upon contact with the target tissue. In this way, accurate and precise implantation of human lubricating gel and/or a drug contained therein can be accomplished in a minimally invasive procedure. The target tissue site includes at least tissue associated with intra-articular joints and cavities associated therewith. The human lubricating gel can further include a therapeutic agent, such as for example an anti-inflammatory agent, an analgesic agent, a skeletal muscle relaxant, an osteoinductive anabolic growth factor, an anti-catabolic growth factor or a combination thereof.

In various embodiments, by utilizing the human lubricating gel, implantation of the drug formulation can now be accomplished without the need to suture the drug formulation to the target site reducing physical and psychological trauma to the patient. In various embodiments, the human lubricating gel is sprayable (utilizes "spray-a-dose" technology) and allows voids in, for example, bones to be filled in so that the drug formulation can be delivered directly to the target tissue site. In various embodiments, when drug formulations are contained in drug depots, the human lubricating gel allows accurate placement of the drug depot in a manner to optimize location, accurate spacing, and drug distribution.

In one exemplary embodiment, a human lubricating gel for delivering a therapeutic agent to a target tissue site beneath the skin of a patient is provided, the human lubricating gel being capable of adhering to the target tissue site and comprising one or more biodegradable drug formulations containing an effective amount of the therapeutic agent, wherein the target tissue site comprises at least one muscle, ligament, tendon, cartilage, spinal disc, spinal foraminal space near the spinal nerve root, facet or synovial joint, or spinal canal.

In another exemplary embodiment, a human lubricating gel for delivering a therapeutic agent to a target tissue site beneath the skin of a patient is provided, the human lubricating gel being capable of adhering to the target tissue site and comprising one or more biodegradable drug formulations containing an effective amount of the therapeutic agent, wherein the target tissue site comprises intra-articular joints, cavities associated with intra-articular joints including sinus cavities.

In another exemplary embodiment, a method is provided for delivering a therapeutic agent into an intra-articular joint such as, for example, a synovial joint of a patient, the method comprising inserting a cannula at or near a target tissue site in the synovial joint and spraying human lubricating gel capable of adhering to the target tissue site in the synovial joint, the human lubricating gel comprising one or more biodegradable drug formulations containing an effective amount of the therapeutic agent.

In yet another exemplary embodiment, a method for delivering a therapeutic agent into a target tissue site beneath the skin is provided, the method comprising inserting a cannula at or near a target tissue site and injecting human lubricating gel, the gel capable of adhering to the target tissue site, the human lubricating gel comprising one or more biodegradable drug formulations containing an effective amount of the therapeutic agent, wherein the target tissue site comprises intra-articular joints, cavities associated with intra-articular joints including sinus cavities.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
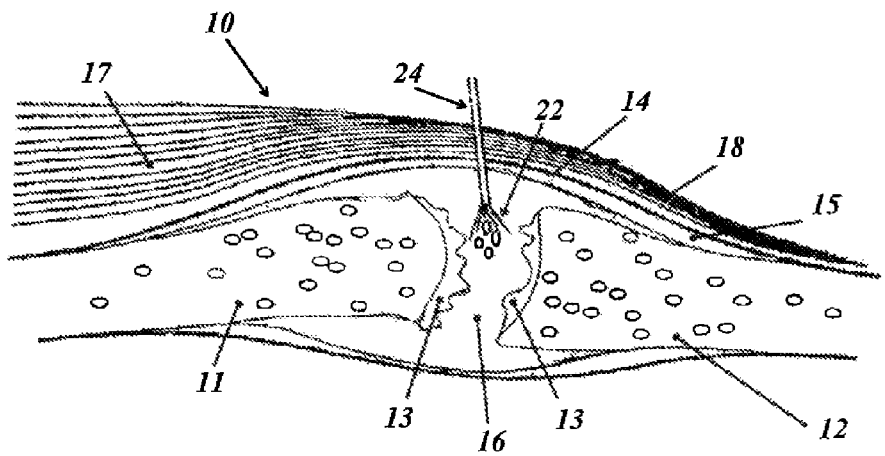
FIG. 1 illustrates a side sectional view of a joint affected by osteoarthritis and delivery of an embodiment of a sprayable human lubricating gel containing a plurality of drug depots inserted into the synovial joint via a cannula or needle.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a gel" includes one, two, three or more gels.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New human gel lubricant, compositions containing and methods of treatment using the same are provided, which can easily allow accurate and precise implantation of a drug with minimal physical and psychological trauma to the patient. The drug compositions and methods provided utilize human gel lubricant that adheres to the target tissue site (intra-articular joint, e.g., synovial joint, etc.), and in various embodiments, hardens on contact with the target tissue site. In this way, accurate and precise application of the human lubricating gel, and in some embodiments the human lubricating gel further comprising a drug, in a minimally invasive procedure can be accomplished. In various embodiments, the human lubricating gel avoids the need to suture the drug depot to the target site reducing physical and psychological trauma to the patient. In various embodiments, when several drug depots are to be implanted, the human lubricating gel allows accurate placement of the drug depot in a manner to optimize location, accurate spacing, and drug distribution. In various embodiments, the drug compositions containing human lubricating gel and methods utilize spray-a-dose technology that allows voids in, for example, bones to be filled in so that the drug compositions containing human lubricating gel can be delivered directly to the target tissue site.

Human Lubricating Gel

Bone is made up of collagen, mineral, and other non-collagenous proteins. As used herein "human lubricating gel" refers to any gel derived by the denaturing of human bone, skin, or other connective tissue. Human bone matrix gelatin (HBMG) comprises collagen and non-collagenous proteins from human bone matrix after the removal of minerals. Human lubricating gel may be prepared by several methods. In one method, HBMG is first processed (for example by ball mill) to form micro/nano particles or fibers. The resulting micro/nano particles or fibers are then homogenized in a buffer solution (the pH should be close to the pH of the targeting tissue environment) to form a gel-like injectable dispersion. In another method, HBMG particles are further treated with a hydrolysis agent to partially hydrolyze or digest the surface. Partially hydrolyzed or digested HBMG particles/fibers form a gel in a buffer solution by homogenization. In one embodiment of the invention, the concentration of the gel is from about 0.1 to about 50% by weight of the total formulation. In another embodiment of the invention, the concentration of the gel is from about 1 to about 5% by weight of the total formulation. The particular concentration of the lubricating gel in the formulation depends on the target tissue environment and may be ascertained by one of ordinary skill in the art utilizing the teachings of this invention.

The primary tissue of bone, osseous tissue, is a relatively hard and lightweight composite material, formed mostly of calcium phosphate called calcium hydroxylapatite (this is the osseous tissue that gives bones their rigidity). Bone has relatively high compressive strength, of about 170 MPa (1800 kgf/cm$^2$) but poor tensile strength of 104-121 MPa and very low shear stress strength (51.6 MPa), meaning it resists pushing forces well, but not pulling or torsional forces. While bone is essentially brittle, it does have a significant degree of elasticity, due primarily to collagen.

Collagen is a group of naturally occurring proteins found in animals, especially in the flesh and connective tissues of mammals. It is the main component of connective tissue, and is the most abundant protein in mammals, making up about 25% to 35% of the whole-body protein content. Over 90% of the collagen in the body is of type I, found in skin, tendon, vascular ligature, organs, bone as the main component of the organic part of bone.

Collagen, in the form of elongated fibrils, is found primarily in fibrous tissues such as tendon, ligament and skin, and is also abundant in cornea, cartilage, bone, blood vessels, the gut, and intervertebral disc. The fibroblast is the most common cell which creates collagen. Gelatin is collagen that has been irreversibly hydrolyzed.

If collagen is sufficiently denatured, e.g., by heating, the tertiary and secondary structure of collagen strands separate partially or completely into globular domains, containing a different secondary structure to the normal collagen polyproline II (PPII), e.g., random coils. This process generally describes the formation of gelatin. For this application, human bone matrix gelatin can be prepared by treating human bones and/or skin with a denaturing agent and/or heat according to methods described by Urist in U.S. Pat. No. 4,294,753, hereby incorporated by reference in its entirety. As used herein a "denaturing agent" refers to a substance which can disrupt the three dimensional structure in macromolecules such as collagen. In some embodiments, denaturing agents include urea and guanidine. The denaturing can be physical (heat, pressure, mechanical force), chemical (reactions or de-crosslinking)) or biological (enzymes such as collagenase, pepsin, ficin etc). It can also be fully or partially to some extent only on the surface.

In various embodiments, the human lubricating gel comprises a drug depot. A drug depot comprises a physical structure to facilitate sustained release of the drug in a desired site (e.g., a synovial joint, a disc space, a spinal canal, a tissue of the patient, etc.). The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent around the depot for delivery to the site. In various embodiments, the drug depot provides an optimal drug concentration gradient of the therapeutic agent at a distance of up to about 1 cm to about 5 cm from the implant site.

A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired.

Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), U0126, Gd, SCID- 469 (Scios), R03201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The human lubricating gel may also contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The human lubricating gel comprises the therapeutic agent or agents and may also contain other non-active ingredients. It has a multi-functional purpose including the carrying, stabilizing and controlling the release of the therapeutic agent (s). The controlled release process, for example, may be by a solution-diffusion mechanism or it may be governed by an erosion-controlled process. Typically, the human lubricating gel semi-solid formulation is comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements.

In various embodiments, the human lubricating gel material will be durable within the tissue site for a period of time equal to (for biodegradable components) or greater than (for non-biodegradable components) the planned period of drug delivery. For example, the human lubricating gel material may have a melting point or glass transition temperature close to or higher than body temperature, but lower then the decomposition or degradation temperature of the therapeutic agent. However, the pre-determined erosion of the human lubricating gel material can also be used to provide for slow release of the loaded therapeutic agent(s).

In various embodiments, the human lubricating gel may have a high drug loading, such that the therapeutic agent comprises about 5-99 wt % of the depot, or 30-95 wt % of the depot, or 50-95 wt % of the depot. The balance is depot material, including optional inactive materials.

In some instance, the human lubricating gel may comprise a biodegradable material. There are numerous materials available for this purpose and having the characteristic of being able to breakdown or disintegrate over a prolonged period of time when positioned at or near the target tissue. As function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

The human lubricating gel may be used as part of and/or carrier for capsules, microspheres, microparticles, microcapsules, microfibers particles, nanospheres, nanoparticles, coating, matrices, wafers, pills, pellets, emulsions, liposomes, micelles, or other pharmaceutical delivery compositions. Suitable materials for these pharmaceuticals forms are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the gel including human lubricating gel will degrade over time by the action of enzymes, by hydrolytic action and/or by other similar mechanisms in the human body. In various embodiments, "biodegradable" include the human lubricating gel and other non-human gel material that can break down or degrade within the body to non-toxic components after or while a therapeutic agent has been or is being released. By "bioerodible" it is meant that the gel including human lubricating gel will erode or degrade over time due, at least in part, to contact with substances found in the surrounding tissue, fluids or by cellular action. By "bioabsorbable" it is meant that the gel including human lubricating gel will be broken down and absorbed within the human body, for example, by a cell or tissue. "Biocompatible" means that the gel including human lubricating gel will not cause substantial tissue irritation or necrosis at the target tissue site.

In various embodiments, the human lubricating gel may comprise a bioabsorbable, a bioabsorbable, and/or a biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The human lubricating gel may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %.

The human lubricating gel and/or compositions containing it may also include optionally physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or metal complexes (e.g., Zn-protein complexes).

The human lubricating gel and/or compositions containing it may be administered by a direct application, by an injection, delivered from a pump, or it may delivered from a preformed device such as a depot for controlled delivery, or any combination thereof. The depot can be different sizes, shapes and configurations. An example of suitable non-limiting designs for a depot is discussed in U.S. Pat. No. 7,741,273 incorporated herein by reference in its entirety.

There are several factors that can be taken into consideration in determining the size, shape and configuration of the drug depot containing and/or contained into human lubricating gel. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet, and the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot or human lubricating gel to permit the user to accurately position the depot or human lubricating gel into the target site of the patient. These radiographic markers will also permit the user to track movement and degradation of the depot or human lubricating gel at the site over time. In this embodiment, the user may accurately position the depot or human lubricating gel in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. In various embodiments, the radiographic marker could be a spherical shape or a ring around the depot.

In other embodiments, the human lubricating gel for delivering a therapeutic agent to a target tissue site beneath the skin of a patient is capable of adhering to the target tissue site and further comprises one or more biodegradable depots containing an effective amount of a therapeutic agent, wherein the target tissue site comprises at least a tissue associated with an intra-articular joint.

Throughout this specification the term "intra-articular joint" is intended to indicate the point at which two or more bones are connected. Generally the opposing surfaces of bone are lined with cartilaginous or fibrous tissue. The types of joints which the method of the present invention relates to include freely movable (diarthrosis) or synovial joints, slightly movable (amphiarthrosis) joints and immovable (synarthrosis) joints. In particular, the present application relates to synovial or freely movable and slightly movable joints.

Freely moving synovial joints are not directly joined, namely the bones have a synovial cavity and are united by the dense irregular connective tissue that forms the articular capsule that is normally associated with accessory ligaments. The term "cavity" is defined as a space within a biological structure that can be filled by a gas or fluid. Examples of cavity would include lumen or tubular cavities such as for example intestinal, digestive, respiratory and ear cavities; socket cavities including orbital, cranial, pleural, pericardial and sinus cavities as well as joint cavities composed of a space between two or more bones. Paranasal sinuses include maxillary, shenoidal, frontal and ethmoid sinuses named according to the bones within which the sinuses lie. The sinuses are lined with soft, pink tissue called mucosa. Normally, the sinuses are empty except for a thin layer of mucus. Occasionally, the sinus cavities experience pathologies caused by, for example, an autoimmune disease, rheumatoid arthritis, degenerative disease, injury, and/or trauma. These pathologies can benefit from treatment with human lubricating bone gel.

Also considered to be within the scope of the term "intra-articular joints" are artificial or prosthetic joints, which may have been implanted into a mammal. Such joints may have been manufactured from stainless steel or other metallic alloys, ceramics, plastics or other suitable materials. It is possible for the joints which the method of the present invention is intended to treat to comprise a wholly artificial implanted joint or in fact merely a partially implanted joint, such as for example the case where a synthetic ball on the head of the femur bone is implanted into a mammal to articulate with the cartilage lined bony socket of the pelvis.

The methods presented in this application are particularly suited to the lubrication of artificial joints as well as to lubrication of joints or other physiological articulations during or after surgical intervention. The reason for this is that human lubrication gel helps in preventing surgical adhesions, which can be a complication of implantation of prosthetic joints or other surgical procedures.

In various embodiments, the human lubricating gel further has gelatinous, jelly-like, or colloidal properties at room temperature. In various embodiments, the human lubricating gel may have the therapeutic agent dispersed throughout it or one or more drug formulations in the form of microspheres, microparticles, microcapsules, microfibers particles, nanospheres, nanoparticles, or mixtures thereof comprising the therapeutic agent may be suspended within the human lubricating gel. The dispersal of the therapeutic agent may be even throughout the human lubricating gel. Alternatively, the concentration of the therapeutic agent may vary throughout it. As the biodegradable material of the human lubricating gel degrades at the site, the therapeutic agent is released.

In another exemplary embodiment, the human lubricating gel in viscous form is loaded with one or more drug formulations (e.g., microspheres, microparticles, microcapsules, microfibers particles, nanospheres, nanoparticles, etc. loaded with a therapeutic agent), wherein the viscous human lubricating gel is positioned into a synovial joint, or a soft tissue surrounding the sinus cavity of a subject. The human lubricating gel can also be used, in various embodiments, to seal or repair tissue. In yet another exemplary embodiment, the human lubricating gel is a sprayable, injectable, and/or an adherent gel that solidifies upon contact with tissue. For example, the human lubricating gel may be administered as a liquid that gels in situ at the target tissue site. In various embodiments, the human lubricating gel can comprise a two part system where a liquid is administered and a gelling agent is added subsequently to cause the liquid to gel or harden.

In various embodiments, the human lubricating gel is a hardening gel, which is separate from the drug formulation and applied before, during or after implantation of the drug formulation. After the human lubricating gel is applied to the target site, it hardens holding the drug formulation in place in this way the need to suture the drug formulation to the target tissue site is avoided.

In various embodiments, the viscous human lubricating gel is loaded with a drug formulation, which delivers the therapeutic agent to the desired target tissue site (e.g., inflamed tissue, degenerative tissue, etc.) and prevents the drug formulation from being removed from that site by the venous systemic circulation or otherwise dispersed too widely, which reduces the desired therapeutic effect. For example, after hours or days, the human lubricating gel may be absorbed, thereby allowing the drug formulations (e.g., microspheres, microparticles, microcapsules, microfibers particles, nanospheres, nanoparticles, etc.) to begin releasing the therapeutic agent. The microspheres may not begin releasing the agent until they are released from the human lubricating gel. So, the microspheres may be formed from insoluble or inert substances, but soluble or active once it comes into contact with the target tissue site. Likewise, the human lubricating gel may comprise a substance that dissolves or disperses within the tissue. As the human lubricating gel begins to dissolve within hours to days, the drug formulations (e.g., microspheres, microparticles, microcapsules, microfibers particles, nanospheres, nanoparticles, etc.) are exposed to body fluids and begin releasing their contents. So, the human lubricating gel may further comprise the same or different material as the drug formulation (e.g., POE, PEG). The human lubricating gel and drug formulation can be formulated to optimize exposure time of the drug and release of the therapeutic agent from the drug formulation.

In various embodiments, the human lubricating gel is flowable and can be injected, sprayed, instilled, and/or dispensed to, on or in the target tissue site. "Flowable" means that the human lubricating gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the human lubricating gel may be used to fill one or more voids in an osteolytic lesion.

In various embodiments, the human lubricating gel further comprises poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly (d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the human lubricating gel in a controlled and/or sustained manner. For example, the human lubricating gel containing the therapeutic agent and a polymer matrix can be injected at the target tissue site and the polymer matrix breaks down over time (e.g., days, months) within the target tissue site releasing the therapeutic agent. Thus the administration of the human lubricating gel can be localized and occur over a period of time (e.g., at least one day to about 3, 6, 9 or 12 months).

The term "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the human lubricating gel and/or drug formulation, or a matrix or component thereof, or as the result of metabolic transformation or dissolution of the therapeutic agent(s) or conjugates of therapeutic agent(s).

In various embodiments, the human lubricating gel and/or drug formulation can be designed to cause an initial burst dose of therapeutic agent within the first 24 hours after implantation. "Initial burst" or "burst effect" or "bolus dose" refers to the release of therapeutic agent from the gel and/or depot during the first 24 hours after the gel comes in contact with an aqueous fluid (e.g., synovial fluid, cerebral spinal fluid, etc.). The "burst effect" could be due to the increased release of therapeutic agent from the human lubricating gel while it is coagulating or hardening to form a solid or semi solid (rubbery) implant, while the gel is still in a flowable state, because of its relatively fast degradation properties, or relatively fast drug diffusion through the gel. In alternative embodiments, the human lubricating gel and/or drug formulations are designed to avoid this initial burst effect.

In various embodiments, the human lubricating gel has a pre-dosed viscosity in the range of about 1 to about 500 centipoise (cps), 1 to about 200 cps, or 1 to about 100 cps. After the human lubricating gel is administered to the target site, the viscosity of the human lubricating gel will increase and the human lubricating gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the human lubricating gel comprises an adherent gel including a therapeutic agent that is evenly distributed throughout the human lubricating gel. The adherent gel may be of any suitable type, as previously indicated, and should be sufficiently viscous so as to prevent the human lubricating gel from migrating from the targeted delivery site once deployed; the human lubricating gel should, in effect, "stick" or adhere to the targeted tissue site. The human lubricating gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the human lubricating gel into an intra-articular joint or on the targeted tissue site, such as, for example, a sinus cavity. The therapeutic agent may be mixed into the human lubricating gel prior to the human lubricating gel being deployed at the targeted tissue site. In various embodiments, the human lubricating gel may be part of a two-component delivery system and when the two components are mixed, a chemical process is activated to form an adherent gel including the human lubricating gel and cause it to stick or adhere to the target tissue. In various embodiments, the human lubricating gel may also adhere to the targeted tissue site by a mechanical interdigitation with the target tissue prior to hardening. In other embodiments, the human lubricating gel may adhere to the target tissue site by chemical bonding of the human lubricating gel to the target tissue site (e.g., ionic bonding, covalent bonding, hydrogen bonding, electrostatic interaction, hydrophobic, hydrophilic or other interaction with target tissue site). In still other embodiments, the human lubricating gel may adhere to the target tissue site by a combination of chemical bonding and mechanical interdigitation.

In various embodiments, a human lubricating gel is provided that hardens or stiffens after delivery. Typically, hardening human lubricating gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening human hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those human lubricating gel formulations that contain a polymer, the polymer concentration may affect the rate at which the human lubricating gel hardens (e.g., a gel with a higher concentration of polymer may coagulate more quickly than gels having a lower concentration of polymer). In various embodiments, when the human lubricating gel hardens, the resulting matrix is solid but is also able to conform to the irregular surface of the tissue (e.g., recesses and/or projections in bone).

The percentage of polymer present in the human lubricating gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the composition containing human lubricating gel can be varied by many methods known in the art. The choice of method to vary molecular weight is typically determined by the composition of the resulting gel (e.g., polymer, versus non-polymer). For example in various embodiments, when the human lubricating gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the human lubricating gel composition is designed to be a flowable gel, it can vary from low viscosity, similar to that of water, to a high viscosity, similar to that of a paste, depending on the molecular weight and concentration of the biodegradable polymer used in the human lubricating gel. The viscosity of the human lubricating gel can be varied such that the polymeric composition can be applied to a patient's tissues by any convenient technique, for example, by brushing, spraying, dripping, injecting, or painting. Different viscosities of the human lubricating gel will depend on the technique used to apply the composition. For example, spraying requires a human lubricating gel composition having a low viscosity.

In various embodiments, the human lubricating gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a human lubricating gel with a high molecular weight provides a stronger matrix and the matrix takes more time to degrade. In contrast, a human lubricating gel with a low molecular weight degrades more quickly and provides a softer matrix. In various embodiments, the human lubricating gel has a molecular weight, as shown by the inherent viscosity, from about 0.10 dL/g to about 1.2 dL/g or from about 0.10 dL/g to about 0.40 dL/g.

In various embodiments, the human lubricating gel can have a viscosity of about 300 to about 5,000 centipoise (cp). In other embodiments, the human lubricating gel can have a viscosity of from about 5 to about 300 cps, from about 10 cps to about 50 cps, from about 15 cps to about 75 cps at room temperature, which allows it to be sprayed at or near the target site. The human lubricating gel may have a viscosity enhancing agent such as, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

The sprayability of the human lubricating gel can also be controlled, among other things, by controlling the particle size distribution of the human lubricating gel components. In various embodiments, the particle size distribution of the drug formulations suspended in the human lubricating gel may be in the range of from about 10 μm to 100 μm so that the human lubricating gel can easily be sprayed at or near the target site.

In contrast to a sprayable gel that typically employs a low viscosity polymer, a human lubricating gel with a higher viscosity may be desirable for other applications, for example, a human lubricating gel having a putty-like consistency may be more preferable for bone regeneration applications. In various embodiments, when a polymer is employed in the human lubricating gel, the polymeric composition includes about 10 wt % to about 90 wt % or about 30 wt % to about 60 wt % of the polymer.

In various embodiments, the human lubricating gel further comprises a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

The human lubricating gel may further be supplemented with other lubricating agents not necessarily present in a human bone matrix gel or resulting from denaturing of human bone and skin. A natural component of synovial fluid, hyaluronic acid (HA) plays an essential part in the viscoelastic properties of synovial fluid, and is thus a natural candidate for a lubricating agent for use together with the human lubricating gel. Another suitable example of the lubricating agent comprises Lubricin which is available from, for example, Affinity BioReagents, Inc. of Golden, Co.

Hyaluronic acid or sodium hyaluronate is a high molecular weight polysaccharide of N-acetyl glucosamine and glucuronic acid molecules that is naturally occurring in all mammals in a variety of tissue and some bacterial species. HA can thus be derived from various animal sources as well as be produced through culture or synthetic assembly methods. For the purposes of this application, hyaluronic acid includes any derivatives such as hyaluronan and hyaluronic acid itself with $H^+$ ion attached to the $COO^-$ group, and salts of hyaluronic acid whereby another positive ion replaces the $H^+$ ion, as for example, with $Na^+$ which forms sodium hyaluronate. Also included in the definition of hyaluronic acid is any physically or chemically cross-linked hyaluronic acid or derivative. Hyaluronic acid polymers are very large with molecular weights of between about 100 and 90,000,000 DA and can displace a large volume of water. In some embodiments HA includes a non-cross linked hyaluronic acid with a molecular weight of 0.5 to 10 M Dalton.

Currently, there are at least five FDA approved HA based products on the market. They include Euflexxa™, Hyalgan®, Synvisc®, Supartz® and Orthovisc®. Any of these products or any combinations thereof may be used as another lubricating agent for the combinations with human lubricating gel described herein. Although hyaluronic acids from other sources are acceptable, for medical purposes it is preferable to use the ones approved by or known to the FDA. The HA solution can be in a range of about 0.05 and about 50% weight per volume.

In various embodiments, rather than directly admixing the therapeutic agent into the human lubricating gel, microspheres may be dispersed within the human lubricating gel, the microspheres loaded with the therapeutic agent. In one embodiment, the microspheres provide for a sustained release of the therapeutic agent. In yet another embodiment, the human lubricating gel, which is biodegradable, prevents the microspheres from releasing the therapeutic agent; the microspheres thus do not release the therapeutic agent until they have been released from the gel. For example, a human lubricating gel may be deployed around a target tissue site (e.g., a nerve root). Dispersed within the human lubricating gel are microspheres that encapsulate the desired therapeutic agent. Certain of these microspheres degrade once released from the human lubricating gel, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention also contemplates the use of adherent gels in addition to the human lubricating gel to so constrain dispersal of the therapeutic agent. These adherent gels may be deployed, for example, in a disc space, in a spinal canal, or in surrounding tissue, or in a joint space, such as a synovial cavity such as, for example, a sinus cavity. In this embodiment the human lubricating gel is an adherent and/or settable gel in order to stay in place within a joint space.

Cannula or Needle

It will be appreciated by those with skill in the art that the human lubricating gel can be administered to the target site using a cannula or needle that can be a part of a drug delivery device e.g., a syringe, a gun drug delivery device, or any medical device suitable for the application of a drug to a targeted organ or anatomic region. The cannula or needle of the drug formulation device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or human lubricating gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, human lubricating gel, and/or medical device to administer the drug may be sterilizable. In various embodiments, one or more components of the drug depot, human lubricating gel, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in the human lubricating gel.

Other methods may also be used to sterilize the human lubricating gel, depot and/or one or more components of the device, including, but not limited to, gas sterilization, such as, for example, with ethylene oxide or steam sterilization.

In various embodiments, a kit is provided which may include additional parts along with the human lubricating gel and/or drug formulation, medical device combined together to be used to implant the human lubricating gel and/or drug formulation. The kit may include the drug formulation device in a first compartment. The second compartment may include a canister holding the human lubricating gel and/or drug formulation to be sprayed at the target site, and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

A set of instructions is also provided in the kit. The set of instructions preferably includes information necessary for proper use of the kit, such as dosage and timing of administration of the composition of the present invention. Optionally, the set of instructions may also provide secondary information concerning, for example, postoperative care and observations of the patients receiving orthopedic implants coated with the composition of the present invention. A person of ordinary skill in the art will appreciate that the set of instructions can be in any suitable medium, including, without limitation, printed, video-taped, digital, and audio-recorded. In addition to English language instructions, instructions in other languages may be provided.

Drug Delivery

In various embodiments, a method for delivering a therapeutic agent into a synovial joint of a patient is provided, the method comprising inserting a cannula at or near a target tissue site in the synovial joint and implanting the drug formulations at the target site beneath the skin of the patient and brushing, spraying, dripping, injecting, or painting the human lubricating gel in the target site to hold or have the drug formulation adhere to the target site. In this way unwanted migration of the drug formulations away from the target site is reduced or eliminated.

In various embodiments, to administer the human lubricating gel having the drug formulation or depot dispersed therein to the desired site, first the cannula or needle can be inserted through the skin and soft tissue down to the target tissue site and the human lubricating gel administered (e.g., brushed, sprayed, dripped, injected, or painted, etc.) at or near the target site. In those embodiments where the drug formulation or depot is separate from the human lubricating gel, first the cannula or needle can be inserted through the skin and soft tissue down to the site of injection and one or more base layer(s) of human lubricating gel can be administered to the target site. Following administration of the one or more base layer(s), the drug formulation or depot can be implanted on or in the base layer(s) so that the human lubricating gel can hold the drug formulation in place or reduce migration. If required a subsequent layer or layers of human lubricating gel can be applied on the drug formulation or depot to surround it and further hold it in place. Alternatively, the drug formulation or depot may be implanted first and then the human lubricating gel placed (e.g., brushed, sprayed, dripped, injected, or painted, etc.) around the drug formulation or depot to hold it in place. By using the human lubricating gel, accurate and precise implantation of a drug formulation or depot can be accomplished with minimal physical and psychological trauma to the patient. The human lubricating gel also avoids the need to suture the drug formulation or depot to the target site reducing physical and psychological trauma to the patient.

In various embodiments, when the target site comprises a joint or spinal region, a portion of fluid (e.g., synovial fluid, spinal fluid, etc.) can be withdrawn from the target site through the cannula or needle first and then the human lubricating gel administered (e.g., brushed, sprayed, dripped, injected, or painted, etc.). The target site will re-hydrate (e.g., replenishment of fluid) and this aqueous environment will cause the drug to be released from the drug formulation, depot or the human lubricating gel.

The human lubricating gel may be used for localized delivery of the therapeutic agent to the patient to treat a disease or condition such as for example, osteoarthritis, rheumatoid arthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like. In various embodiments, the gel may also be used to repair tissue as well deliver a therapeutic agent. The human lubricating gel is especially useful in treating or lubricating pathological conditions associated with the sinus cavity.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drug depots, human lubricating gels or microspheres, microparticles, microcapsules, microfibers particles, nanospheres, nanoparticles, or mixtures thereof dispersed in the human lubricating gel having a quantity of therapeutic agent that can be deposited at or near the target site as needed for treatment of pain, inflammation or other disease or condition.

In various embodiments, the human lubricating gel may be used to treat rheumatoid arthritis (RA) and/or osteoarthritis by inserting a cannula at or near a target tissue site and implanting the drug formulation or depot at the target site beneath the skin of the patient and brushing, spraying, dripping, injecting, or painting the human lubricating gel at the target site to hold or have the drug formulation or depot adhere to the target site. In this way unwanted migration of the drug formulation or depot away from the target site is reduced or eliminated.

RA is a chronic systemic disease characterized by progressive joint deformity and joint destruction in which cytokines play a central pathogenic role. The clinical course of RA is variable and often shows a remitting pattern. Three forms of RA can be distinguished: mild, self-limiting disease; mildly progressive disease; and aggressive disease, which are difficult to control with medication, and are characterized by functional decline and radiologic deterioration of the joints, e.g., joint space narrowing and erosions. In accordance with the systemic nature of RA, there are extra-articular manifestations, which include vasculitis, alveolitis, and ocular disease. Onset of RA is often insidious with fatigue, anorexia, generalized weakness, and vague musculoskeletal symptoms. Specific symptoms appear later. Several joints, usually in a symmetrical fashion, are affected. Most often these are joints of the hands, wrists, knees, and feet. Joints are painful and swollen, and motion is limited. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Laboratory findings may include elevation of erythrocyte sedimentation rate (ESR) and C-reactive protein (CRP) along with rheumatoid factor. Rheumatoid factor is an autoantibody against the Fc portion of IgG found in more than two-thirds of all patients. High titers of rheumatoid factor are a good indicator of disease activity. Mild anemia (normochromic, normocytic) and eosinophilia may be present as well. With progression of the disease, X-ray abnormalities such as general deformity, juxta-articular osteopenia, loss of articular cartilage, and bone erosion become more evident.

In one exemplary embodiment, the human lubricating gel is utilized to treat osteoarthritis (OA), which is the most common form of arthritis in Western populations. Knee OA, characterized clinically by pain and functional disability, is the leading cause of chronic disability among the elderly in the US. Risk factors for OA include age, gender, race, trauma, repetitive stress/joint overload, muscle weakness, and genetic factors. Pathologically, the most striking changes in OA are focal loss of articular cartilage and marginal and central new bone formation. However, OA is not simply a disease of articular cartilage and the subchondral bone. Rather, it is a disease of the synovial joint, with alterations also found in the synovium, capsule, ligaments, periarticular muscle, and sensory nerves.

Although OA was once considered a non-inflammatory arthropathy, patients often present with signs and symptoms consistent with local inflammation and synovitis, and inflammation and inflammatory mediators play a role in the joint destruction associated with OA as well as in pain. Both chondrocytes and synovium in OA can produce proinflammatory cytokines, including IL-1β, which can alter cartilage homeostasis in favor of cartilage degradation. For example, IL-1β appears to be a major factor stimulating matrix metalloproteinase synthesis and other cartilage catabolic responses in OA.

FIG. 1 illustrates one embodiment of the effect of osteoarthritis on the joint 10. Osteoarthritis causes the cartilage 13 to become worn away from the ends of the bones 11, 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11, 12 stable and allow the joint 10 to bend and move. However, symptoms become worse and debilitating as the disease progresses. To treat the diseased joint, the human lubricating gel 22 can be administered locally at the target site utilizing a cannula or needle 24 that penetrates beneath the skin to the target site 22. In this embodiment, the human lubricating gel 22 contains the drug formulation suspended in it and the gel is sprayed at the target site (shown at or near the osteolytic lesions). It will be understood that some synovial fluid 16 may be withdrawn from the joint 10 and the human lubricating gel added before, during, or after the synovial fluid is withdrawn so that as the joint re-hydrates, the therapeutic agent will be released as the fluid contacts the drug formulation. The human lubrication gel may also be placed at other target sites (e.g., by the meniscus or cartilage surface) and the drug released. In this way, accurate and precise implantation of a drug formulation in a minimally invasive procedure can be accomplished. In various embodiments, the human lubricating gel avoids the need to suture the drug formulation to the target site reducing physical and psychological trauma to the patient. In various embodiments, when several drug formulations or depots are to be implanted, the human lubricating gel allows accurate placement of the drug formulation in a manner to optimize location, accurate spacing, and drug distribution.

Figure 2:
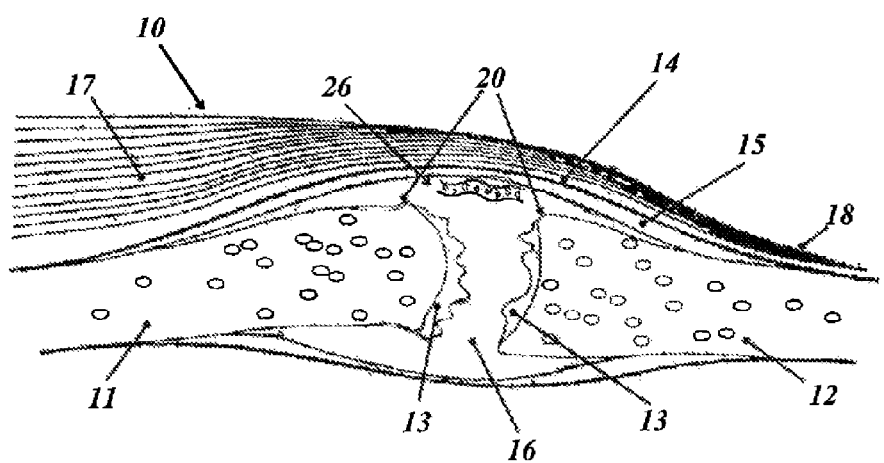
FIG. 2 illustrates a side sectional view of a joint affected by osteoarthritis and delivery of an embodiment of a human lubricating gel containing a plurality of drug depots, which adheres and hardens after contact with the target tissue, in this case, a synovial joint.

FIG. 2 illustrates one embodiment of the effect of osteoarthritis on the joint 10. Osteoarthritis causes the cartilage 13 to become worn away from the ends of the bones 11 and 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11 and 12 stable and allow the joint 10 to bend and move. However, symptoms become worse and debilitating as the disease progresses. To treat the diseased joint, the human lubricating gel can be administered locally at the target site utilizing a cannula or needle that penetrates beneath the skin to the target site. In this embodiment, the human lubricating gel comprises the drug formulation or depot suspended in the human lubricating gel and the human lubricating gel is sprayed near the target site (shown near the osteolytic lesions). In this embodiment, the human lubricating gel has adhering and hardening characteristics 26 and adheres and hardens in an area that does not interfere with movement of the joint and is away from the articular surfaces of the joint. As the synovial fluid contacts the hardening human lubricating gel, the therapeutic agent suspended therein is released.

Figure 3:
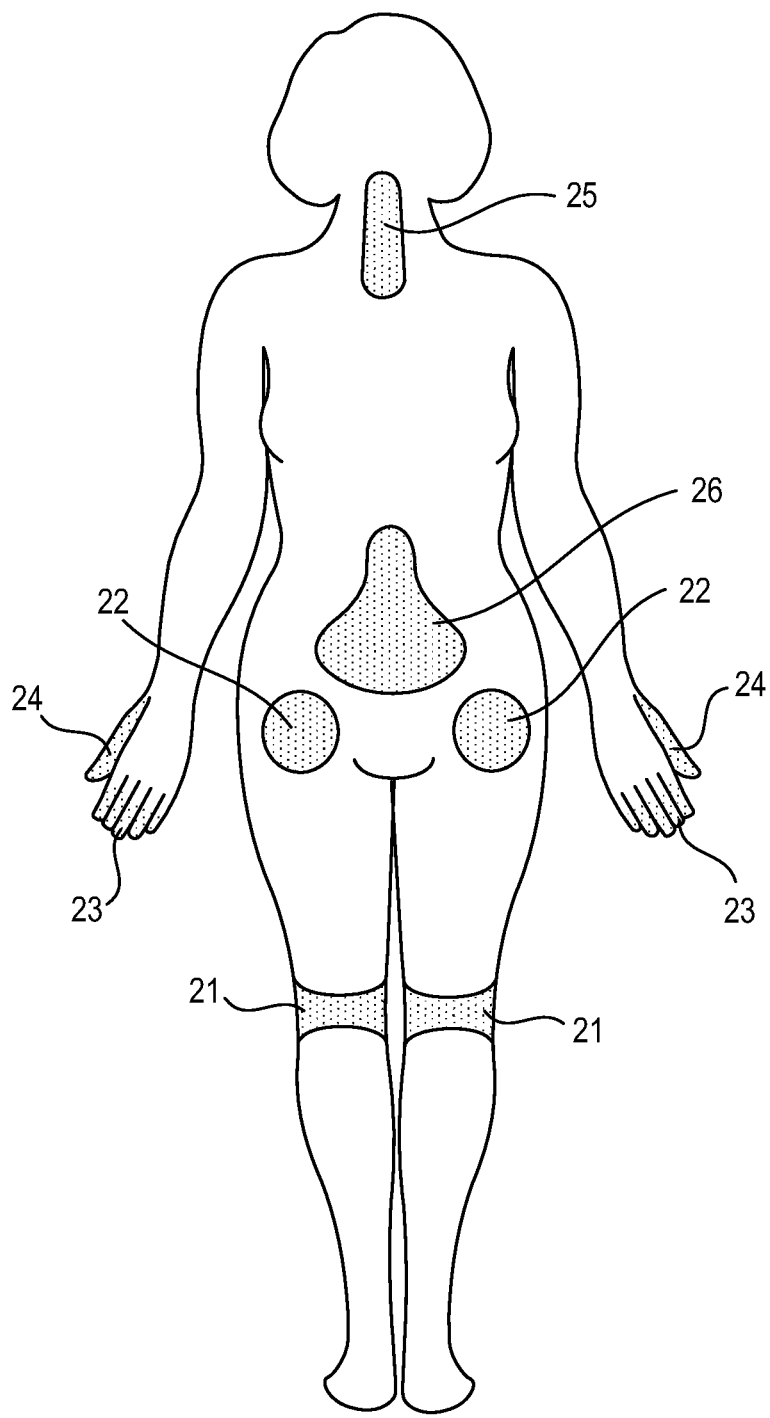
FIG. 3 illustrates a number of common locations within a patient that may be affected by osteoarthritis and locations that the human lubricating gel can locally be administered thereto and used to fill voids in bone.

FIG. 3 illustrates a number of common locations within a patient that may be affected by osteoarthritis. It will be recognized that the locations illustrated in FIG. 3 are merely exemplary of the many different locations within a patient that may be affected by osteoarthritis. For example, osteoarthritis may affect a patient's knees 21, hips 22, fingers 23, thumbs 24, neck 25, and spine 26. Osteoarthritis in the hips 22 can cause pain, stiffness, and severe disability. Patients may feel the pain in their hips 22, groin, inner thigh, buttocks, or knees.

Osteoarthritis in the fingers 23 may cause the fingers 23 to become enlarged and gnarled. The disease may cause small, bony knobs to appear on the end joints of the fingers 23. These knobs are referred to as Heberden's nodes. Similar knobs, called Bouchard's nodes, can appear on the middle joints of the fingers 23. Affected fingers 23 may ache or be stiff and numb. More women than men suffer from osteoarthritis in the fingers 23, and they develop it especially after menopause. The base of the thumb joint 24 may also be similarly affected by osteoarthritis.

Osteoarthritis in the neck 25 and spine 26 may cause stiffness and pain in the neck or in the lower back. It may also cause weakness or numbness of the arms or legs. Osteoarthritis in the neck 25 and spine 26 is often debilitating and may result in the patient being bed-ridden. To treat the diseased sites of osteoarthritis, the human lubricating gel can be administered locally at the target sites discussed above utilizing a cannula or needle that penetrates beneath the skin to the target site.

In various embodiments, the human lubricating gel is used to treat or manage pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

The term "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

As described above, the human lubricating gel can be used to deliver a drug formulation to any site beneath the skin, including, but not limited to, at least one muscle, ligament, tendon, cartilage, synovial joint, spinal disc, spinal foraminal space, near the spinal nerve root, facet joint, or spinal canal.

In various embodiments, the human lubricating gel may have the therapeutic agent suspended therein and deployed around a targeted tissue site (e.g., a nerve root). The human lubricating gel, either viscous or solid once deployed, keeps the therapeutic agent closely bound to target site (e.g., a nerve root) providing a therapeutically effective dosage of the therapeutic agent to the target site, with the dosage gradient rapidly falling off outside of the region of the human lubricating gel. The therapeutic agent is therefore tightly targeted to the desired tissue site.

It will be apparent to those skilled in the art that various modifications and variations can be made to various embodiments described herein without departing from the spirit or scope of the teaching herein. Thus, it is intended that various embodiments cover other modifications and variations of various embodiments within the scope of the present teachings.

What is claimed is:

1. A human lubricating gel for delivering lubrication to a target tissue site beneath the skin of a patient, the human lubricating gel obtained from denatured collagen and being capable of adhering to the target tissue site, the human lubricating gel having a modulus of elasticity in a range of about $1 \times 10^4$ to about $6 \times 10^5$ dynes/cm$^2$ after delivery to the target tissue, the human lubricating gel comprising human bone matrix gelatin in an amount of from about 0.1 to about 50% by weight based on a total weight of the gel, wherein the target tissue site comprises at least tissue associated with an intra-articular joint.

2. A human lubricating gel according to claim 1, further comprising a therapeutic agent, wherein the therapeutic agent comprises an anti-inflammatory agent, an analgesic agent, a skeletal muscle relaxant, an osteoinductive anabolic growth factor, an anti-catabolic growth factor or a combination thereof.

3. A human lubricating gel according to claim 2, wherein the target tissue site is the tissue lining the sinus cavity.

4. A human lubricating gel according to claim 2, wherein the human lubricating gel is sprayable and hardens after contacting the target tissue site.

5. A human lubricating gel according to claim 2, wherein the human lubricating gel further comprises a bolus dose of the therapeutic agent suspended in the human lubricating gel to provide an immediate release of the therapeutic agent and the effective amount of the therapeutic agent is encapsulated in the plurality of microparticles, microspheres, microcapsules, microfibers, particles, nanospheres, nanoparticles or mixtures thereof to provide sustained release of the therapeutic agent over time.

6. A human lubricating gel according to claim 2, wherein the human lubricating gel further comprises polyethylene glycol.

7. A human lubricating gel according to claim 2, wherein the human lubricating gel further comprises a hydrogel.

8. A human lubricating gel according to claim 2, wherein the human lubricating gel further comprises a radiographic marker adapted to assist in radiographic imaging, the radiographic marker comprises barium, calcium, and/or metal beads.

9. A method for delivering a human lubrication gel according to claim 1 into an intra-articular joint comprising a fibrous joint, a cartilaginous joint or a synovial joint of a patient, the method comprising inserting a cannula at or near a target tissue site in the intra-articular joint and spraying the human lubricating gel, the gel being capable of adhering to the target tissue site in the intra-articular joint.

10. A method for delivering a human lubricating gel according to claim 9, wherein the human lubricating gel further comprising an effective amount of a therapeutic agent.

11. A method for delivering a human lubricating gel according to claim 9, wherein the human lubricating gel hardens after contacting the target tissue site.

12. A method for delivering a human lubricating gel according to claim 10, wherein the therapeutic agent comprises an anti-inflammatory agent, an analgesic agent, a skeletal muscle relaxant, an osteoinductive anabolic growth factor, an anti-catabolic growth factor or a combination thereof.

13. A method for delivering a human lubricating gel according to claim 10, wherein the therapeutic agent is encapsulated in a plurality of microparticles, microspheres, microcapsules, microfibers, particles, nanospheres, nanoparticles or mixtures thereof suspended in the human lubricating gel.

14. A method for delivering a human lubricating gel according to claim 13, wherein the human lubricating gel further comprises a bolus dose of the therapeutic agent suspended in the human lubricating gel to provide an immediate release of the therapeutic agent and the effective amount of the therapeutic agent is encapsulated in the plurality of microspheres, microcapsules, microfibers, particles, nanospheres, nanoparticles or mixtures thereof to provide sustained release of the therapeutic agent over time.

15. A method for delivering a human lubricating gel according to claim 9, wherein the human lubricating gel comprises polyethylene glycol or a hydrogel.

16. A method for delivering a therapeutic agent according to claim 9, wherein the target tissue site comprises at least tissue associated with an intra-articular joint.

17. A method for delivering a therapeutic agent according to claim 9, wherein the target tissue site comprises at least the tissue lining the sinus cavity.

18. A method for delivering a therapeutic agent into a target tissue site beneath the skin, the method comprising inserting a cannula at or near a target tissue site and injecting a human lubricating gel according to claim 1 capable of adhering to the target tissue site, the human lubricating gel comprising a plurality of microspheres, microcapsules, microfibers, particles, nanospheres, nanoparticles or mixtures thereof and containing an effective amount of the therapeutic agent, wherein the target tissue site comprises at least the tissue lining the sinus cavity.

19. A method for delivering a therapeutic agent according to claim 18, wherein the therapeutic agent comprises an anti-inflammatory agent, an analgesic agent, a skeletal muscle relaxant, an osteoinductive anabolic growth factor, anti-catabolic growth factor or a combination thereof.

* * * * *